United States Patent [19]

Glass et al.

[11] Patent Number: 4,828,820

[45] Date of Patent: May 9, 1989

[54] CHEWABLE TOOTH CLEANING COMPOSITION

[75] Inventors: Michael Glass, Fairlawn, N.J.; Kenneth P. Bilka, Franklin Square; Anthony Guzowski, Maspeth, both of N.Y.

[73] Assignee: Warner-Lambert Company, Morris Plains, N.J.

[21] Appl. No.: 3,670

[22] Filed: Jan. 15, 1987

[51] Int. Cl.[4] .................. A61K 9/68; A61K 33/10
[52] U.S. Cl. ...................... 424/48; 424/440; 424/687; 426/3
[58] Field of Search .............. 424/48, 49, 156; 426/34, 56

[56] References Cited

U.S. PATENT DOCUMENTS

| | | | |
|---|---|---|---|
| 1,171,392 | 2/1916 | Meier | 424/48 |
| 3,590,120 | 6/1971 | Muhler | 424/48 |
| 3,966,863 | 6/1976 | Forward et al. | 424/52 |
| 3,974,293 | 8/1976 | Witzel | 426/4 |
| 4,029,760 | 6/1977 | De Roeck et al. | 424/48 |
| 4,065,579 | 12/1977 | Mackay et al. | 426/3 |
| 4,102,992 | 7/1978 | Davis | 424/49 |
| 4,157,387 | 6/1979 | Benedict | 424/54 |
| 4,238,475 | 12/1980 | Witzel et al. | 424/48 |
| 4,248,894 | 2/1981 | Mackay et al. | 426/3 |
| 4,265,877 | 5/1981 | Tenta | 426/3 |
| 4,317,837 | 2/1982 | Kehoe et al. | 426/3 |
| 4,317,838 | 3/1982 | Cherukurl et al. | 426/5 |
| 4,352,822 | 10/1982 | Cherukurl et al. | 426/4 |
| 4,357,354 | 11/1982 | Kehoe et al. | 426/3 |
| 4,357,355 | 11/1982 | Koch et al. | 426/4 |
| 4,387,108 | 6/1983 | Koch et al. | 426/4 |
| 4,400,372 | 8/1983 | Muhler et al. | 424/48 |
| 4,565,691 | 1/1986 | Jackson | 424/49 |
| 4,587,120 | 5/1986 | Ozawa | 424/57 |

OTHER PUBLICATIONS

Ansel Introduction to Pharmaceutical Dosage Forms (1969) pp. 265-266.

Primary Examiner—Shep K. Rose
Attorney, Agent, or Firm—Anne M. Kelly; Daniel A. Scola, Jr.

[57] ABSTRACT

A chewable tooth cleaning composition which removes dental plaque from the chewing surfaces of the teeth has incorporated into a chewing gum formulation about 20% to about 40% by weight, based on the weight of the total composition, of a calcium carbonate abrasive having a specific particle size distribution.

20 Claims, No Drawings

1

CHEWABLE TOOTH CLEANING COMPOSITION

FIELD OF THE INVENTION

The present invention relates to a chewable tooth cleaning composition which removes dental plaque from the chewing surfaces of the teeth. More particularly, this invention relates to a chewable tooth cleaning composition containing about 20% to about 40% by weight, based on the weight of the total composition, of a calcium carbonate abrasive having a specific particle size distribution.

BACKGROUND OF THE INVENTION

The use of calcium carbonate as an abrasive in toothpaste and in tooth powders is well known in the art. For example, U.S. Pat. No. 3,966,863, to G. C. Forward et al., discloses an oral hygiene composition having anti-cariogenic activity containing an ionic fluoride, an ionic monofluorophosphate and a calcium carbonate abrasive having a median diameter of less than 40 microns.

U.S. Pat. No. 4,102,992, to W. B. Davis, discloses a dentifrice containing a calcium carbonate cleaning agent in particle size form having a weight median diameter of 10 to 15 microns and, in addition, a polymeric material, such as polymethylmethacrylate, having a particle size of 40 to 100 microns, which polymeric material reduces the abrasivity of the calcium carbonate.

U.S. Pat. No. 4,587,120, to T. Ozawa et al., discloses dentifrice compositions containing calcium hydrogen phosphate anhydride whose crystallite has an average size of about 300 to about 3,500 angstroms, as measured by X-ray diffractometry, which are claimed to have improved cleaning action without an increase in abrasiveness.

U.S. Pat. No. 4,029,760, to Y. De Roeck et al., discloses a dentifrice composition containing carragheenan as a gingivitis-controlling agent, and other usual dentifrice ingredients, including powdered calcium carbonate as the abrasive material.

The prior art discussed above indicates that calcium carbonate or other abrasives have been included in dentifrice preparations, with a specified particle size dependent upon the abrasive material selected and the other ingredients present. However, in practice, calcium carbonate included in dentifrice compositions as an abrasive generally has a particle size between 1 and 10 microns in order to observe abrasivity limitations recognized in good dental practice.

It is also well known in the art that mineral adjuvants such as calcium carbonate are added to chewing gum compositions to act as fillers or to provide non-stick properties. Thus, for example, U.S. Pat. No. 4,357,355, to E. Koch et al., discloses a non-stick bubble gum base composition that contains about 5% to about 25% by weight of calcium carbonate.

A number of chewing gum compositions have been disclosed in the art which are said to inhibit or reduce plaque in the oral cavity. For example, U.S. Pat. Nos. 4,148,872, 4,150,112, 4,156,715, 4,156,716, 4,157,385, 4,159,315, 4,160,054, 4,160,820, 4,161,517, and 4,170,632, all to A. Wagenknecht et al., disclose chewing gum compositions effective in inhibiting or reducing plaque in the oral cavity. These chewing gum compositions contain a chewing gum base and a surface active agent, and, in some instances, a zinc compound or a plaque inhibiting flavor. In addition, a calcium carbonate abrasive may be included in the aforementioned chewing gum compositions.

U.S. Pat. No. 4,400,372, to J. C. Muhler et al., discloses a chewing gum composition containing a chewing gum base, at least one non-toxic source of an acid and calcined kaolin particles having a median diameter of 2 micrometers of less, wherein substantially all of the kaolin particles are less than 20 micrometers in diameter.

U.S. Pat. No. 3,590,120, to J. C. Muhler, discloses a chewing gum composition containing an insoluble gum base; zirconium silicate particles as a cleaning and polishing agent, wherein at least 20% by weight of said particles are up to about 3 microns in size and between 5% and 40% by weight are about 10 to about 20 microns in size; and a dental plaque removing agent which may be sodium carbonate, sodium bicarbonate, or chloroform.

Although calcium carbonate has been used as a mineral adjuvant or filler in chewing gum compositions, calcium carbonate used for this purpose is generally of a particle size ranging from about 3 microns to about 12 microns. In addition, the particle size of the agents specified in the plaque inhibiting chewing gum compositions cited above range in size from about 2 microns or less to about 20 microns. Thus, it is quite surprising that the chewable tooth cleaning composition of the present invention, containing calcium carbonate having a particle size distribution such that about 44% of the particles, based on the total weight of calcium carbonate, are larger than about 74 microns, is effective in removing plaque from the chewing surfaces of the teeth without abrasive damage to or scratching of the tooth surfaces.

SUMMARY OF THE INVENTION

This invention relates to a chewable tooth cleaning composition which removes plaque from the chewing surfaces of the teeth comprising about 19% to about 30% by weight, based on the weight of the total composition, of a gum base; about 2.15% to about 16.2% by weight of at least one plasticizing/softening agent; about 22.05% to about 65.3% by weight of at least one sweetening agent; about 0.6% to about 3% by weight of at least one flavoring agent; and about 20% to about 40% by weight of a calcium carbonate abrasive having the following particle size distribution: about 0.03% by weight, based on the total weight of the calcium carbonate, having a particle size larger than about 420 microns; about 10% by weight having a particle size larger than about 250 microns; about 34% by weight having a particle size larger than about 149 microns; about 44% by weight having a particle size larger than about 74 microns; and about 11.97% by weight having a particle size smaller than about 74 microns. The chewable tooth cleaning composition of this invention is prepared by melting a suitable gum base and adding thereto, with mixing, the calcium carbonate particles and at least one plasticizing/softening agent. Next, at least one sweetening agent, and one or more flavoring agents are added and mixing is continued until a homogenous mixture is obtained.

This invention also relates to a method for removing plaque from the chewing surfaces of the teeth which comprises regularly chewing the chewable tooth cleaning composition of this invention.

DETAILED DESCRIPTION OF THE INVENTION

It has been found that, by incorporating a specific particle size and level of calcium carbonate into a chewing gum, a chewable tooth cleaning composition is obtained. Moreover, calcium carbonate of the particle size specified, when incorporated into a chewing gum composition at the critical concentration specified, provides a good abrasive which will not damage the tooth enamel upon prolonged usage. By chewing the chewable tooth cleaning composition of this invention on a regular basis, plaque is removed from the chewing surfaces of the teeth by the action of the calcium carbonate particles.

The calcium carbonate suitable for use in the practice of this invention is commercially available from White Pigment Corporation, Florence, Vt., and is known as Veroc 40/200, which has the following particle size distribution: about 0.03% by weight of the calcium carbonate particles have a particle size larger than about 420 microns; about 10% by weight have a particle size larger than about 250 microns; about 34% by weight have a particle size larger than about 149 microns; about 44% by weight have a particle size larger than about 74 microns; and about 11.97% by weight have a particle size smaller than about 74 microns.

Calcium carbonate having the above stated particle size is incorporated into a chewing gum composition in an amount of about 20% to about 40%, preferably about 20% to about 25% by weight, based on the weight of the total composition, will provide a chewable tooth cleaning composition which is effective in removing plaque from the chewing surfaces of the teeth without damage to the dental enamel, even after prolonged usage.

The chewing gum used in the chewable tooth cleaning composition of this invention is preferably a sugarless chewing gum since sugarless gums do not promote tooth decay. However, sugar containing chewing gums may also be used. Chewing gum formulations are well known in the art and typically contain, in addition, to a chewing gum base, one or more plasticizing/softening agents; at least one sweetening agent and at least one flavoring agent.

Thus, the chewable tooth cleaning composition of this invention contains the following ingredients, in percent by weight, based on the weight of the total composition:

| Ingredient | Amount | Preferred Amount |
|---|---|---|
| Gum base | 19.0%–30.0% | 24.0%–28.0% |
| Plasticizing/Softening Agent | 2.15%–16.2% | 7.5%–9.9% |
| Sweetening Agent | 22.05%–65.3% | 34.18%–48.22% |
| Flavoring Agent | 0.6%–3.0% | 1.8%–2.2% |
| Calcium Carbonate* | 20.0%–40.0% | 20.0%–25.0% |

*Particle size distribution as specified above.

Gum base materials suitable for use in the practice of this invention are well known in the art and include natural or synthetic gum bases or mixtures thereof. Representative natural gums or elastomers include chicle, natural rubber, jelutong, balata, guttapercha, lechi caspi, sorva, guttakay, crown gum, perillo, or mixtures thereof. Representative synthetic gums or elastomers include butadiene-styrene copolymers, polyisobutylene and isobutylene-isoprene copolymers. Among these, butadienestyrene copolymers, polyisobutylene, isobutylene-isoprene copolymers or mixtures thereof, are frequently used. Further descriptions of suitable chewing gum bases are found in U.S. Pat. No. 4,357,355, to E. Koch et al., U.S. Pat. No. 4,387,108, to E. Koch et al., and U.S. Pat. No. 4,518,615, to S. R. Cherukuri et al., all of which are herein incorporated by reference. The preferred chewing gum base is described in U.S. Pat. No. 4,518,615.

Plasticizing/softening agents commonly used in chewing gum compositions are suitable for use in the practice of this invention, including lanolin, propylene glycol, glycerol, acetylated monoglyceride, glyceryl triacetate, glyceryl diacetate, fatty acids, lecithin, glycerin, and the like and mixtures thereof. In a preferred embodiment of this invention, a combination of acetylated monoglyceride, lecithin and glycerin is used, generally in amounts of about 0.05% to about 0.5% acetylated monoglyceride, about 0.1% to about 0.7% lecithin and about 2.0% to about 15.0% glycerin; preferably about 0.1% to about 0.3% acetylated monoglyceride, about 0.4% to about 0.6% lecithin and about 7.0% to about 9.0% glycerin, percents being by weight, based on the weight of the total chewable tooth cleaning composition.

The sweetening agent ingredient used in the practice of this invention may be selected from a wide range of materials, including water-soluble sweeteners, water-soluble artificial sweeteners, and dipeptide based sweeteners, including mixtures thereof. Without being limited to particular sweetening agents, representative illustrations encompass:

A. Water-soluble sweeteners such as monosaccharides, disaccharides, and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof;

B. Water-soluble artificial sweeteners such as the soluble saccharin salts, i.e., sodium or calcium saccharin salts, cyclamate salts, such as the sodium salt and the like, and the free acid form of saccharin; dipeptide based sweetening agents such as L-aspartyl-L-phenyl-alanine methyl ester and materials described in U.S. Pat. No. 3,492,131 and the like; dihydrochalcone; glycyrrhizin; Stevia rebaudiana (Stevioside); and the synthetic sweetener 3,6-dihydro-6-methyl-1,1,2,3-oxathiazin-4-one-2,2-dioxide, particularly the potassium (Acesulfame-K), sodium and calcium salts thereof, as described in German Pat. No. 2,001,017.7.

The water-soluble sweeteners described in Category A above are preferably used in amounts of about 22.05% to about 65.3% by weight, and most preferably from about 34.18% to about 48.22% by weight, based on the weight of the total composition.

In those instances where the sweetening agent chosen does not provide bulk or texture, such as where the artificial sweeteners of Category B above are used, the term sweetening agent, for purposes of this invention, is meant to include artificial sweeteners and bulk sweeteners. Typical bulk sweeteners such as one or more sugar alcohols, including sorbitol, mannitol, xylitol and the like, or mixtures thereof, are utilized in amounts of about 22% to about 65%, preferably about 34% to about 48% by weight, together with one or more of the artificial sweeteners described in Category B above, which artificial sweeteners are utilized in amounts of about 0.05% to about 0.3%, preferably about 0.18% to about 0.22%, by weight, all percentages being based on the weight of the total composition.

In a preferred embodiment of this invention, the sweetening agent used is a combination of an artificial sweetener such as sodium saccharin, and bulk sweeteners such as mannitol and sorbitol, generally in amounts of about 0.05% to about 0.3%, preferably about 0.18% to about 0.22% artificial sweetener; about 2% to about 15%, preferably about 4% to about 8% mannitol; and about 20% to about 50%, preferably about 30% to about 40% sorbitol, all percentages being by weight, based on the weight of the total chewable tooth cleaning composition. Although the sugarless chewable tooth cleaning composition is preferred, the sweetening agent used in the practice of this invention may include sugar as well as an artificial sweetener.

The combination of artificial sweeteners and bulk sweeteners used in this invention generally provides approximately equivalent levels of bulk and sweetness as do the saccharide type of sweeteners in category A above. Thus, about 22.05% to about 65.3%, preferably about 34.18% to about 48.22% by weight of one or more sweetening agents, based on the weight of the total chewable tooth cleaning composition, are used in the practice of this invention. The amounts of sweetening agents described above are ordinarily necessary to achieve a desired level of sweetness independent of the flavor level achieved from the inclusion of flavoring agents.

One or more flavoring agents, in liquid, powder or encapsulated form, are used in the chewable tooth cleaning composition of this invention. A variety of flavors known in the art may be used, including essential oils, such as cinnamon, spearmint, peppermint, menthol, birch, anise and the like; natural fruit flavors derived from the essence of fruits, such as apple, pear, peach, strawberry, cherry, apricot, orange, watermelon, banana and the like; bean-derived flavors, such as coffee, cocoa and the like; wine-derived flavors, such as curacao zin and the like; and pungent materials, such as affinin, pepper, mustard and the like.

In addition to the ingredients listed above, the gum compositions may also include conventional additives such as antioxidants, preservatives, colorants, and the like. For example, titanium dioxide may be utilized as a colorant, and an antioxidant such as butylated hydroxytoluene, butylated hydroxyanisole, propyl gallate, and mixtures thereof, may also be included.

Naturally, the gum bases may be prepared for a variety of products, including conventional gums and bubble gums, and the invention is not limited to a specific gum base formulation. The above description of typical ingredients is therefore presented for purposes of illustration only.

The chewable tooth cleaning composition of this invention is prepared by melting the gum base material to a temperature of between about 80° C. and about 90° C. To the melted chewing gum base there is added calcium carbonate abrasive particles having the critical particle size distribution specified above, at least one plasticizing/softening agent and an artificial sweetener, if a sugarless gum formulation is being prepared. Next, one or more flavoring agents and bulk sweeteners (or sugar-containing sweeteners, in the case of a sugar-containing gum) are added, together with additional plasticizing/softening agents, if desired, and mixing is continued until a homogeneous mixture is obtained. The mixture is then pressed into the form desired, typically into rectangular gum sticks weighing approximately 3 grams each.

In order to obtain the efficacious, organoleptically acceptable, chewable tooth cleaning composition of this invention, it is critical to add the calcium carbonate particles to the melted gum base, along with at least one, or a portion of, the plasticizing/softening agent, with mixing, during the initial preparation of the composition. This order of addition ensures that the calcium carbonate particles are intimately admixed with the gum base, which will reduce the gritty texture of the composition and avoid damage to the tooth enamel.

A representative chewable tooth cleaning composition in accordance with the practice of this invention contains about 19% to about 30% by weight, based on the weight of the total composition, of a gum base; a combination plasticizing/softening agent comprising about 0.05% to about 0.5% by weight of acetylated monoglyceride, about 0.1% to about 0.7% by weight of lecithin, and about 2% to about 15% by weight of glycerin; a combination sweetening agent comprising about 2% to about 15% of mannitol, about 20% to about 50% by weight of sorbitol, and about 0.05% to about 0.3% by weight of sodium saccharin; about 0.6% to about 3% by weight of a flavoring agent; and about 20% to about 40% by weight of calcium carbonate particles having the following particle size distribution: about 0.03% by weight of the particles, based on the total weight of the calcium carbonate, have a particle size larger than about 420 microns; about 10% by weight have a particle size larger than about 250 microns; about 34% by weight have a particle size larger than about 149 microns; about 44% by weight have a particle size larger than about 74 microns; and about 11.97% by weight have a particle size smaller than about 74 microns.

In a preferred embodiment, the chewable tooth cleaning composition of this invention contains about 24% to about 28% by weight, based on the weight of the total composition, of a gum base; a combination plasticizing/softening agent comprising about 0.1% to about 0.3% by weight of acetylated monoglyceride, about 0.4% to about 0.6% by weight of lecithin and about 7% to about 9% by weight of glycerin; a combination sweetening agent comprising about 4% to about 8% by weight of mannitol, about 30% to about 40% by weight of sorbitol, and about 0.18% to about 0.22% by weight of sodium saccharin; about 1.8% to about 2.2% by weight of a flavoring agent; and about 20% to about 25% by weight of calcium carbonate particles having the following particle size distribution: about 0.03% by weight of the particles, based on the total weight of the calcium carbonate, have a particle size larger than about 420 microns; about 10% by weight have a particle size larger than about 250 microns; about 34% by weight have a particle size larger than about 149 microns; about 44% by weight have a particle size larger than about 74 microns; and about 11.97% by weight have a particle size smaller than about 74 microns.

The following examples are given to illustrate the invention, but are not deemed to be limiting thereof. All percentages given throughout the specification are based upon weight, unless otherwise indicated.

EXAMPLE 1

The chewable tooth cleaning composition of the invention is prepared from the following ingredients:

| Ingredient | Amount (Grams) |
| --- | --- |
| 1. Gum Base | 1300.0 |
| 2. Acetylated Monoglyceride | 10.0 |
| 3. Lecithin | 25.0 |
| 4. Mannitol | 200.0 |
| 5. Sorbitol | 1955.0 |
| 6. Mint Flavor | 57.5 |
| 7. Menthol Crystals USP (flavor) | 42.5 |
| 8. Glycerin USP | 400.0 |
| 9. Sodium Saccharin, Spray Dried | 10.0 |
| 10. Calcium Carbonate, Abrasive* | 1000.0 |

*Veroc 40/200, White Pigment Corporation, Florence, Vermont, with the following particle size distribution: 0.03% by weight, based on the total weight of the calcium carbonate, have a particle size larger than 420 microns; 10% by weight have a particle size larger than 250 microns; 34% by weight have a particle size larger than 149 microns; 44% by weight have a particle size larger than 74 microns; and 11.97% by weight have a particle size smaller than about 74 microns.

Gum base ingredient #1 is melted at a temperature of 85° C. The plasticizing/softening agents #2 and #3, the sodium saccharin #9 and calcium carbonate abrasive #10 are added, with mixing for approximately 2 minutes. Flavor ingredients #6 and #7 are pre-blended. The pre-blended flavors and the remaining ingredients, #4 and #5 (bulk sweeteners) and #8 (plasticizing/softening agent) are then added to the gum base mixture and mixing is continued for 8–10 minutes. The resulting mixture is then pressed into rectangular sticks of gum weighing 3.2 grams each.

EXAMPLE 2

A comparative chewable tooth cleaning composition is prepared from the following ingredients, following the procedure of Example 1:

| Ingredient | Amount (Grams) |
| --- | --- |
| 1. Gum Base Compound | 1300.0 |
| 2. Acetylated Monoglyceride | 10.0 |
| 3. Lecithin | 25.0 |
| 4. Mannitol | 200.0 |
| 5. Sorbitol | 1955.0 |
| 6. Mint Flavor | 57.5 |
| 7. Menthol Crystals USP (flavor) | 42.5 |
| 8. Glycerin USP | 400.0 |
| 9. Sodium Saccharin, Spray Dried | 10.0 |
| 10. Calcium Carbonate, Abrasive* | 1000.0 |

*Duramite, White Pigment Corporation, Florence, Vermont, having the following particle size distribution: 50% by weight, based on the total weight of the calcium carbonate, have a particle size between 12 microns and 44 microns, and 50% by weight have a particle size smaller than 12 microns.

EXAMPLE 3

A comparative chewable tooth cleaning composition is prepared from the following ingredients, following the procedure of Example 1:

| Ingredient | Amount (Grams) |
| --- | --- |
| 1. Gum Base Compound | 1300.0 |
| 2. Acetylated Monoglyceride | 10.0 |
| 3. Lecithin | 25.0 |
| 4. Mannitol | 200.0 |
| 5. Sorbitol | 1955.0 |
| 6. Mint Flavor | 57.5 |
| 7. Menthol Crystals USP (flavor) | 42.5 |
| 8. Glycerin USP | 400.0 |
| 9. Sodium Saccharin, Spray Dried | 10.0 |
| 10. Calcium Carbonate, Abrasive* | 500.0 |
| 11. Calcium Carbonate, Abrasive** | 500.0 |

*Veroc 40/200 - See Example 1 for particle size
**Duramite - See Example 2 for particle size

EXAMPLE 4

A comparative chewable tooth cleaning composition is prepared from the following ingredients, following the procedure of Example 1:

| Ingredient | Amount (Grams) |
| --- | --- |
| 1. Gum Base Compound | 1300.0 |
| 2. Acetylated Monoglyceride | 10.0 |
| 3. Lecithin | 25.0 |
| 4. Mannitol | 200.0 |
| 5. Sorbitol | 2455.0 |
| 6. Mint Flavor | 57.5 |
| 7. Menthol Crystals USP (flavor) | 42.5 |
| 8. Glycerin USP | 400.0 |
| 9. Sodium Saccharin, Spray Dried | 10.0 |
| 10. Calcium Carbonate, Abrasive* | 500.0 |

*Veroc 40/200 - See Example 1 for particle size

EXAMPLE 5

A comparative chewable tooth cleaning composition is prepared from the following ingredients, following the procedure of Example 1:

| Ingredient | Amount (Grams) |
| --- | --- |
| 1. Gum Base Compound | 1300.0 |
| 2. Acetylated Monoglyceride | 10.0 |
| 3. Lecithin | 25.0 |
| 4. Mannitol | 200.0 |
| 5. Sorbitol | 2455.0 |
| 6. Mint Flavor | 57.5 |
| 7. Menthol Crystals USP (flavor) | 42.5 |
| 8. Glycerin USP | 400.0 |
| 9. Sodium Saccharin, Spray Dried | 10.0 |
| 10. Calcium Carbonate, Abrasive* | 250.0 |
| 11. Calcium Carbonate, Abrasive** | 250.0 |

*Veroc 40/200 - See Example 1 for particle size
**Duramite - See Example 2 for particle size

EXAMPLE 6

A chewable composition is prepared from the following ingredients, without the calcium carbonate abrasive, following the procedure of Example 1, to serve as a placebo in the comparative tests of Example 8:

| Ingredient | Amount (Grams) |
| --- | --- |
| 1. Gum Base Compound | 1300.0 |
| 2. Acetylated Monoglyceride | 10.0 |
| 3. Lecithin | 25.0 |
| 4. Mannitol | 200.0 |
| 5. Sorbitol | 2955.0 |
| 6. Mint Flavor | 57.5 |
| 7. Menthol Crystals USP (flavor) | 42.5 |
| 8. Glycerin USP | 400.0 |
| 9. Sodium Saccharin, Spray Dried | 10.0 |

EXAMPLE 7

A commercially available plaque-fighting chewing gum composition containing the following ingredients was used in the comparative tests of Example 8 (amounts of ingredients not provided, except for sodium saccharin):

1. Sorbitol
2. Gum Base
3. Zirconium Silicate
4. Glycerin
5. Mannitol

6. Natural and Artificial Flavors
7. Sodium Saccharin—2.3 mg/tablet

Each chewing gum piece weighted approximately 3.2 to 3.3 grams.

ple 4 was not clinically tested since the product of Example 3, also containing 10% coarse calcium carbonate, provided sufficient information on the percentage of plaque removal.

TABLE I

| Example | Abrasive | *% Plaque Removal | Overall | Mintiness | Sweetness | Texture | Grittiness |
|---|---|---|---|---|---|---|---|
| 1 | 20% Coarse CaCO3 | **14.60 | 5.39 | 5.19 | 5.46 | 5.70 | 4.65 |
| 2 | 20% Fine CaCO3 | 9.94 | 5.86 | 5.44 | 5.80 | 6.24 | 6.49 |
| 3 | 10% Coarse CaCO3 10% Fine CaCO3 | 8.86 | 5.37 | 5.17 | 5.22 | 5.57 | 4.92 |
| 4 | 10% Coarse CaCO3 | — | 5.53 | 5.33 | 5.60 | 5.91 | 4.88 |
| 5 | 5% Coarse CaCO3 5% Fine CaCO3 | 8.53 | 5.42 | 5.24 | 5.34 | 5.84 | 5.46 |
| 6 | No CaCO3 (Placebo) | 6.84 | 6.12 | 5.73 | 5.81 | 6.34 | 6.60 |
| 7 | ZrSiO4 (Commercial Product) | 5.11 | 5.74 | 5.87 | 5.82 | 5.20 | 6.50 |

*Clinical Results
**Significantly Different From Placebo

EXAMPLE 8

A double-blind, controlled clinical study was conducted to determine the degree to which experimental chewable tooth cleaning compositions containing mild abrasives reduce accumulated dental plaque, compared to a no-abrasive control chewing gum.

The inventive chewable tooth cleaning composition of Example 1 was compared with the comparative products of Examples 2, 3 and 5; with the control product (without the abrasive ingredient) of Example 6; and with the commercially available plaque-fighting chewing gum of Example 7.

A minimum of 20 generally healthy male and female subjects ages 18–55 who demonstrated extensive plaque on the posterior teeth following disclosure with erythrosin were selected. Subjects had at least six sound functionally occluding posterior teeth (molars and premolars) on each side to participate. Third molars, orthodontically banded, grossly carious or unopposed teeth were excluded from the count. Subjects with gross oral pathology or on antibiotic, antibacterial or antiinflammatory therapy were also excluded.

Subjects abstained from toothbrushing, flossing, gum chewing and any other oral hygiene measures for two days prior to each chewing gum evaluation. A breath spray was provided for ad lib use.

On the morning of the third day, subjects were examined for baseline plaque and were assigned a coded chewing gum. Subjects were instructed to chew the gum vigorously for 10 minutes; plaque was then reevaluated. This protocol was repeated until each subject had evaluated all six coded chewing gums, with several days of normal oral hygiene between each test period.

Disclosed plaque was scored on the buccal and lingual/palatal surfaces of the scorable molar and premolar teeth. The total tooth surface, i.e., buccal or lingual/palatal, was scored by estimating, in increments of 10, the percentage of the surface covered with disclosed plaque.

Subjects were also asked to evaluate the chewable products of Examples 1–7 organoleptically, with respect to overall taste, mintiness, sweetness, texture and grittiness, using an evaluation scale within the following ratings:
1 represented dislike
5 represented a midpoint rating
9 represented liked.

The results of the clinical study and the organoleptic evaluations are listed in Table I. The product of Example 4 was not clinically tested since the product of Example 3, also containing 10% coarse calcium carbonate, provided sufficient information on the percentage of plaque removal.

Results of the clinical study and the organoleptic evaluations reported in Table I indicate that the inventive chewable tooth cleaning composition of Example 1, which contained coarse calcium carbonate, significantly removed more plaque (14.6%) from the chewing surfaces of the teeth than did (a) the placebo of Example 6, which contained no abrasive and removed only 6.8% plaque; or (b), the commercially available product of Example 7, which contained a zirconium silicate abrasive and removed only 5.11% plaque.

Moreover, the results in Table I demonstrate the criticality of the particle size distribution and the concentration of calcium carbonate present in the inventive chewable tooth cleaning composition of Example 1. The comparative chewable tooth cleaning compositions of Examples 2, 3 and 5 did not provide significant removal of plaque when compared to the placebo of Example 6: an equivalent amount of the fine calcium carbonate of Example 2 did not work; an equivalent amount of a combination of half coarse and half fine calcium carbonate, as in Example 3, did not work; and lower levels of a combination of coarse and fine calcium carbonate, as in Example 5, did not work. Neither chewing gum containing equivalent levels of fine calcium carbonate nor chewing gum containing lower levels of coarse combined with fine calcium carbonate demonstrate plaque removal activity significantly greater than that of chewing gum without calcium carbonate.

Therefore, it is quite surprising and totally unexpected that a critical concentration and particle size distribution of calcium carbonate, as claimed in the chewable tooth cleaning compositions of this invention, does provide significant plaque removal from the chewing gum surfaces of the teeth.

Furthermore, results in Table I also indicate that the inventive chewable tooth cleaning composition of Example 1 containing coarse calcium carbonate in an amount sufficient to provide significant plaque removal, has acceptable organoleptic qualities.

Thus, the above comparative examples demonstrate the unpredictability and criticality of calcium carbonate abrasives in chewing gum, and that critical amounts thereof, of a specific particle size, are required to obtain significant plaque removal as well as acceptable organoleptic characteristics.

The invention being thus described, it will be obvious that the same may be varied in many ways. Such variations are not to be regarded as a departure from the scope and spirit of the invention and all such modifications are intended to be included within the scope of the following claims.

What is claimed is:

1. A chewable tooth cleaning composition which removes plaque from the chewing surfaces of the teeth comprising:
   (a) about 19% to about 30% by weight, based on the weight of the total composition, of a gum base;
   (b) about 2.15% to about 16.2% by weight of at least one plasticizing/softening agent;
   (c) about 22.05% to about 65.3% by weight of at least one sweetening agent;
   (d) about 0.6% to about 3% by weight of at least one flavoring agent; and
   (e) about 20% to about 40% by weight of a calcium carbonate abrasive having the following particle size distribution:
      (1) about 0.03% by weight, based on the total weight of the calcium carbonate, having a particle size larger than about 420 microns;
      (2) about 10% by weight having a particle size larger than about 250 microns;
      (3) about 34% by weight having a particle size of larger than about 149 microns;
      (4) about 44% by weight having a particle size larger than about 74 microns; and
      (5) about 11.97% by weight having a particle size smaller than about 74 microns.

2. The composition according to claim 1 wherein the gum base is present in an amount of about 24% to about 28% by weight, based on the weight of the total composition.

3. The composition according to claim 1 wherein the plasticizing/softening agent is present in an amount of about 7.5% to about 9.9% by weight, based on the weight of the total composition.

4. The composition according to claim 1 wherein the plasticizing/softening agent is a combination of acetylated monoglyceride, present in an amount of about 0.05% to about 0.5% by weight; lecithin, present in a amount of about 0.1% to about 0.7% by weight; and glycerin, present in an amount of about 2% to about 15% by weight, all percentages being based on the weight of the total composition.

5. The composition according to claim 1 wherein the sweetening agent is present in an amount of about 34.18% to about 48.22% by weight, based on the weight of the total composition.

6. The composition of claim 1 wherein the sweetening agent is a combination of mannitol, present in an amount of about 2% to about 15% by weight; sorbitol, present in an amount of about 20% to about 50% by weight; and an artificial sweetener, present in an amount of about 0.05% to about 0.3% by weight, all percentages being based on the weight of the total composition.

7. The composition according to claim 6 wherein the artificial sweetner is sodium saccharin.

8. The composition according to claim 1 wherein the flavoring agent is present in an amount of about 1.8% to about 2.2% by weight, based on the weight of the total composition.

9. The composition according to claim 1 wherein the calcium carbonate is present in an amount of about 20% to about 25% by weight, based on the weight of the total composition.

10. A chewable tooth cleaning composition which removes plaque from the chewing surfaces of the teeth comprising:
    (a) about 19% to about 30% by weight, based on the weight of the total composition, of a gum base;
    (b) about 0.05% to about 0.5% by weight of acetylated monoglyceride;
    (c) about 0.1% to about 0.7% by weight of lecithin;
    (d) about 2% to about 15% by weight of glycerin;
    (e) about 2% to about 15% of a mannitol bulk sweetener;
    (f) about 20% to about 50% by weight of a sorbitol bulk sweetener;
    (g) about 0.05% to about 0.3% of sodium saccharin;
    (h) about 0.6% to about 3% by weight of a flavoring agent; and
    (i) about 20% to about 40% by weight of a calcium carbonate abrasive having the following particle size distribution:
       (1) about 0.03% by weight, based on the total weight of the calcium carbonate, having a particle size larger than about 420 microns;
       (2) about 10% by weight having a particle size larger than about 250 microns;
       (3) about 34% by weight having a particle size of larger than about 149 microns;
       (4) about 44% by weight having a particle size larger than about 74 microns; and
       (5) about 11.97% by weight having a particle size smaller than about 74 microns.

11. A chewable tooth cleaning composition which removes plaque from chewing surfaces of teeth comprising:
    (a) about 24% to about 28% by weight, based on the weight of the total composition, of a gum base;
    (b) about 0.1% to about 0.3% by weight of acetylated monoglyceride;
    (c) about 0.4% to about 0.6% by weight of lecithin;
    (d) about 7% to about 9% of glycerin;
    (e) about 4% to about 8% of a mannitol bulk sweetener;
    (f) about 30% to about 40% by weight of a sorbitol bulk sweetener;
    (g) about 0.18% to about 0.22% by weight of sodium saccharin;
    (h) about 1.8% to about 2.2% by weight of a flavoring agent; and
    (i) about 20% to about 25% by weight of a calcium carbonate abrasive having the following particle size distribution:
       (1) about 0.03% by weight, based on the total weight of the calcium carbonate, having a particle size larger than about 420 microns;
       (2) about 10% by weight having a particle size larger than about 250 microns;
       (3) about 34% by weight having a particle size of larger than about 149 microns;
       (4) about 44% by weight having a particle size larger than about 74 microns; and
       (5) about 11.97% by weight having a particle size smaller than about 74 microns.

12. A method for removing plaque from the chewing surfaces of the teeth which comprises chewing, on a regular basis, the composition of claim 1.

13. A method for removing plaque from the chewing surfaces of the teeth which comprises chewing, on a regular basis, the composition of claim 10.

14. A method for removing plaque from the chewing surfaces of the teeth which comprises chewing, on a regular basis, the composition of claim 11.

15. A method for preparing a chewable tooth cleaning composition which comprises:
 1. melting a chewing gum base to a temperature of about 80° C. to about 90° C.;
 2. adding to the melted chewing gum base, with mixing, calcium carbonate abrasive particles and at least one plasticizing/softening agent, said calcium carbonate abrasive having the following particle size distribution: about 0.03% by weight of the calcium carbonate particles have a particle size larger than about 420 microns; about 10% by weight have a particle size larger than about 250 microns; about 34% by weight have a particle size larger than about 149 microns; about 44% by weight have a particle size larger than about 74 microns; and about 11.97% by weight have a particle size smaller than about 74 microns;
 3. adding to the mixture of Step 2 at least one sweetener and at least one flavoring agent, and mixing until a homogeneous mixture is obtained; and
 4. pressing the mixture of Step 3 into the form desired.

16. The method according to claim 15 wherein, in Step 2, there is additionally present an artificial sweetening agent.

17. The composition of claim 1 wherein said calcium carbonate abrasive was added to a melted gum base during prepared of said composition.

18. The compositon of claim 10 wherein said calcium carbonate abrasive was added to a melted gum base during preparation of said composition.

19. The composition of claim 11 wherein said calcium sarbonate abrasive was added to a melted gum base during preparation of said composition.

20. A chewable tooth cleaning composition which removes plaque from the chewing surfaces of teeth prepared by the process of claim 15.

* * * * *